United States Patent [19]

Speck et al.

[11] 4,364,921
[45] Dec. 21, 1982

[54] NOVEL TRIIODINATED ISOPHTHALIC ACID DIAMIDES AS NONIONIC X-RAY CONTRAST MEDIA

[75] Inventors: Ulrich Speck; Peter Blaszkiewicz; Dieter Seidelmann; Erich Klieger, all of Berlin, Fed. Rep. of Germany

[73] Assignee: Schering, Aktiengesellschaft, Berlin & Bergkamen, Fed. Rep. of Germany

[21] Appl. No.: 127,613

[22] Filed: Mar. 6, 1980

[30] Foreign Application Priority Data

Mar. 8, 1979 [DE] Fed. Rep. of Germany ....... 2909439

[51] Int. Cl.³ .................. A61K 49/04; C07H 3/00; C07C 103/78
[52] U.S. Cl. .................................. 424/5; 564/153
[58] Field of Search ............... 260/558 A, 559 A; 424/5; 564/153

[56] References Cited

U.S. PATENT DOCUMENTS 3,701,771 10/1972 Almen et al. ............... 260/211 R
4,001,323 1/1977 Felder et al. ............... 260/559 A
4,021,481 5/1977 Almen et al. ............... 424/5 X
4,107,286 8/1978 Tilly et al. ............... 424/5
4,250,113 2/1981 Nordal et al. ............... 564/153
4,314,055 2/1982 Hoey et al. ............... 564/153 X

FOREIGN PATENT DOCUMENTS 1436357 5/1976 United Kingdom .
1548594 7/1979 United Kingdom .

Primary Examiner—Thomas A. Waltz
Attorney, Agent, or Firm—Millen & White

[57] ABSTRACT

New triiodinated isophthalic acid diamides of the formula

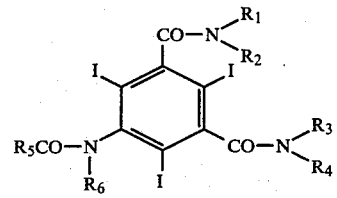

wherein
the amide residues —CO—N.R₁R₂ and —CO—N.R₃R₄ are different from each other and
R₁ is hydrogen or $C_{1-6}$ alkyl,
R₂ is mono- or polyhydroxyalkyl,
R₃ is hydrogen or $C_{1-6}$ alkyl,
R₄ is mono- or polyhydroxyalkyl,
R₅ is $C_{1-6}$ alkyl or mono- or polyhydroxy-$C_{1-6}$-alkyl or $C_{1-3}$-alkoxy-$C_{1-3}$-alkyl, and
R₆ is hydrogen, $C_{1-6}$ alkyl or mono- or polyhydroxyalkyl provide superior nonionic X-ray contrast media.

15 Claims, No Drawings

NOVEL TRIIODINATED ISOPHTHALIC ACID DIAMIDES AS NONIONIC X-RAY CONTRAST MEDIA

BACKGROUND OF THE INVENTION

The present invention relates to nonionic X-ray contrast media.

For a satisfactory portrayal of the organs of the urinary tract, the vascular system, the cerebrospinal cavities and other systems, X-ray contrast media must be administered in high dosage. Accordingly, highly concentrated contrast media solutions are required. In turn, the physicochemical properties of these solutions, such as solubility, viscosity, and osmotic pressure, are of great importance. It is possible, for example, for highly concentrated, nonionic contrast media solutions to exhibit, due to their low osmotic pressure, markedly advantageous compatibility over ionic contrast media solutions. Furthermore, X-ray contrast media for angiography, urography, myelography, etc., must be extraordinarily highly water-soluble.

Metrizamide (U.S. Pat. No. 3,701,771) can be cited as the first, well compatible, soluble, nonionic opacifying compound suitable for practical radiology. In metrizamide, solubility is due, just as for ioglunide (GB No 1,436,357) to a polyhydroxyalkyl residue joined via an acid amide bond to a triiodinated aromatic. Compounds of this type, in addition to being difficult to manufacture, are not sufficiently stable for sterilization under heat, and also have an inadequate shelf life. These properties are a grave disadvantage for their practical use in X-ray contrast media.

Also, among the known derivatives based on triiodaminophthalic acid amides, only a very few proved to be of sufficient compatibility and chemical stability for use as opacifiers in X-ray contrast media for intravasal application. In these compounds, the amide groups in the 1- and 3-positions are substituted symmetrically, i.e., both carboxy groups are amidated with the same amine. (U.S. Pat. No. 4,001,323 and GB Pat. No. 1,548,594).

SUMMARY OF THE INVENTION

Accordingly, it is an object of this invention to provide new X-ray contrast media eliminating the foregoing advantages and satisfying the requirements of effective and safe contrast media.

Upon further study of the specification and appended claims, further objects and advantages of this invention will become apparent to those skilled in the art.

These objects have been attained by this invention by providing new triiodinated isophthalic acid diamides of the formula (I)

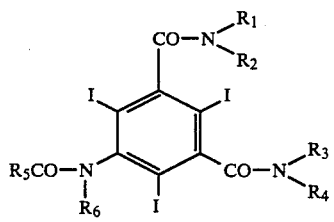

wherein
the amide residues —CO—N.$R_1R_2$ and —CO—N.$R_3R_4$ are different from each other, $R_1$ is hydrogen or lower alkyl,
$R_2$ is straight-chain or branched, mono- or polyhydroxyalkyl,
$R_3$ is hydrogen or lower alkyl,
$R_4$ is straight-chain or branched, mono- or polyhydroxyalkyl,
$R_5$ is lower alkyl, hydroxy lower alkyl or lower alkoxy-lower alkyl, and
$R_6$ is hydrogen or optionally hydroxylated lower alkyl.

DETAILED DISCUSSION

All lower alkyl residues defined above contain 1–6 carbon atoms. $R_1$, $R_3$ and $R_6$ lower alkyl groups contain preferably 1–4 carbon atoms. Preferred examples are methyl, ethyl and propyl. Methyl is most preferred.

The alkyl residue $R_6$ can also be hydroxylated. One to three hydroxy groups in the alkyl residue are preferred. Preferred examples are hydroxyethyl and dihydroxypropyl.

The alkyl residue in the mono- or polyhydroxyalkyl residues $R_2$ and $R_4$ can be of any chain length, e.g., 1–8 carbon atoms, and can be straight-chain or branched. Preferred are alkyl residues of 2–8, most preferably of 2–4 carbon atoms. The hydroxy groups in the alkyl residues can be present as primary and/or secondary and/or tertiary hydroxy groups. The alkyl residues can contain 1–5, preferably 1–3 hydroxy groups. Examples of $R_2$ and $R_4$ include: tris(hydroxymethyl)methyl, hydroxyethyl, especially dihydroxypropyl.

The residue $R_5$ can be a lower alkyl residue, preferably of 1–4 carbon atoms. Methyl is most preferred. If the residue $R_5$ is hydroxylated, it can contain preferably 1–4 carbon atoms in the alkyl residue and carry 1–3 hydroxy groups, preferably one hydroxy group. Examples of hydroxylated alkyl residues $R_5$ include dihydroxypropyl and, preferably, hydroxyethyl and hydroxymethyl. If the alkyl residue $R_5$ is alkoxylated, it can contain 1–3, preferably one, carbon atom in the alkyl residue and 1–3, preferably 1–2, carbon atoms in the alkoxy residue. Particularly preferred is methoxymethyl.

It has now been found in this invention that the aforementioned disadvantages of the prior art media can be entirely avoided or at least markedly reduced if the amide nitrogens in the 1- and 3-positions are differently substituted, as required in Formula I, i.e., if the combinations $R_1R_2$ and $R_3R_4$ are different. The difference in substitution on these amide nitrogens does not refer solely to differences in $R_2$ and $R_4$. It can also be advantageous in connection with the present invention for the substituents $R_1$ and $R_3$ to be different from each other. Thus, $R_1$ can be different from $R_3$ while $R_2$ and $R_4$ are identical, or vice versa, or $R_1$ can be different from $R_3$ when $R_2$ and $R_4$ are also different.

The present invention furthermore concerns a process for the preparation of the compounds of Formula I, comprising, in a conventional manner (a) initially reacting a compound of Formula IIA

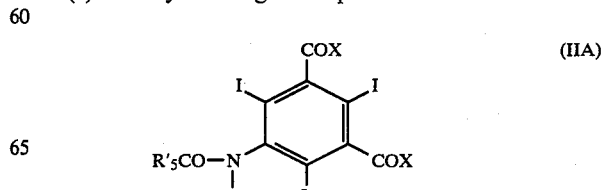

wherein

R'₅=R₅ as defined above but the free hydroxy groups present in the alkyl residue can optionally be functionally modified, R'₆=R₆ as defined above but the free hydroxy groups present in the alkyl residue can optionally be functionally modified, and X is a reactive acid residue or ester residue, with a base of Formula III

  (III)

wherein

R₁ is hydrogen or a lower alkyl residue and

R'₂=R₂ as defined above but hydroxy groups present in the alkyl residue can optionally be functionally modified, and then reacting the thus-obtained 5-[R'₅—CO—(R'₆)—amino]-2,4,6-triiodoisophthalic acid (R'₂—N—R₁) amide chloride with a base of Formula IV

  (IV)

wherein

R₃ is hydrogen or a lower alkyl residue

R'₄=R₄ as defined above but the free hydroxy groups present in the alkyl residue can optionally be functionally modified, and, optionally, thereafter N-alkylating the aromatic acylamino group with an R'₆-containing alkylating agent and/or saponifying a blocked hydroxy group(s) (R'₆=R₆ wherein any free hydroxy groups present are functionally blocked)

(b) N-acylating a compound of Formula IIB

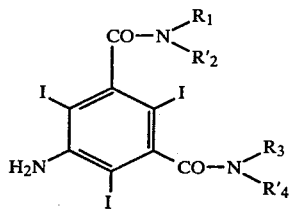  (IIB)

wherein

R₁ and R₃ are as defined above and

R'₂ and R'₄=R₂ and R₄ as defined above but the free hydroxy groups present in their alkyl residues can be functionally modified, with a reactive R'₅-acid derivative (R'₅=R₅ wherein free hydroxy groups present are functionally blocked), and, optionally, thereafter N-alkylating with an R'₆-containing alkylating agent, and/or liberating blocked hydroxy groups or (c) reacting a compound of Formula IIC

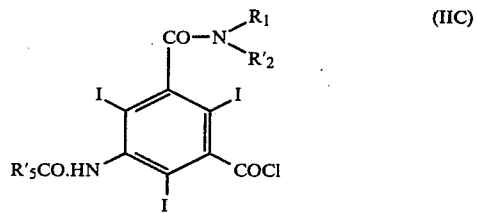  (IIC)

wherein R₁, R'₂ and R'₅ are as defined above, with a base of Formula IV and thereafter optionally N-alkylating with an R'₆-containing alkylating agent and/or liberating blocked hydroxy groups.

Especially suitable as the reactive acid or ester residue X in the starting compound IIA is a halogen, such as —Cl, —Br or —I. The conversion of IIA→I, however, can also be accomplished if X is an azide residue, alkoxycarbonyloxy or the residue of a reactive ester group, e.g., a conventional —O-alkoxy, —O-aryl or —O—CH₂≡N group suitable for such reactions. The conversion of IIA→I is preferably conducted with initial compounds of Formula IIA wherein X is Cl.

For this amidation reaction, hydroxy groups present as the substitutents R'₅ and R'₆ can be in the free or blocked form. When these hydroxy groups are in blocked form, all hydroxy blocking groups conventionally employed for intermediary hydroxy group protection are suitable, i.e., those which can be easily introduced and subsequently easily split off with the regeneration of the finally desired free hydroxy group. Blockage by esterification is preferred, for example, by introducing a benzoyl or acyl residue, especially the acetyl residue. Suitable blocking groups also include ether groups, e.g., benzyl, di- and triphenylmethyl ether groups, as well as acetal and ketal groups with, for example, acetaldehyde and acetone.

The amidation of the two carboxy groups in the 1- and 3-positions takes place stepwise. The two amidation reactions occur in a suitable solvent at 0°–100° C., preferably at 20°–80° C. Suitable solvents include, inter alia, polar solvents. Examples include water, dioxane, tetrahydrofuran, dimethylformamide, dimethylacetamide, hexametapol, and similar compounds, and mixtures thereof. Since the amidation reaction takes place exothermally, it is optionally advantageous to slightly cool the reaction mixture in order to maintain the reaction temperature at about 50° C. Since hydrogen chloride is liberated in the amidation reaction, it must be bound for neutralizing purposes. Two equivalents of a base are required per acid chloride group, suitably in an excess of about 10%. For the practical conductance of this step, the dissolved starting compound IIA is reacted in a first stage with 2 equivalents of base III or with one equivalent of base III and one equivalent of a base different from III which then serves as a proton acceptor.

To avoid secondary reactions during further processing, the monoamide is suitably isolated in conventional fashion and reacted in a second stage analogously with a base IV to obtain the diamide. If the first amidation stage with base III takes place in the presence of a proton acceptor, the second amidation stage with base IV can optionally also be conducted in a single-reactor process without isolation of the primarily formed monoamide.

Advantageous proton acceptors for neutralizing the hydrogen chloride formed during the amidation include tertiary amines, such as, for example, triethylamine, tributylamine or pyridine.

The inorganic or organic salts obtained during the course of the reaction are conventionally separated, advantageously, for example, using a customary ion-exchange column or by filtration over conventional adsorbents, such as, for example, "Diaion" or "Amberlite XAD-2" and "4".

An N-alkylation of the 5-acylamino group to introduce the $R_6$ residue likewise can be accomplished according to methods known to those skilled in the art, e.g., by reacting the diamide in an alkaline solution with the corresponding $R'_6$-alkyl halogenide, preferably $R'_6$-alkyl bromide, at room temperature.

If the course of the reaction makes it necessary to intermediarily block any free hydroxy groups present as substituents $R_2$ and/or $R_4$ and/or $R_5$ and/or $R_6$, this can be done according to conventional methods using easily reversible groups. The introduction of such blocking groups can be accomplished, for example, by esterification (e.g., introduction of preferably an acetyl residue or benzoyl residue) or by etherification (e.g., introduction of the triphenylmethyl residue). The blocking of the hydroxy groups can also be effected by ketalization or acetalization, e.g., by means of acetaldehyde, acetone or dihydropyran.

The subsequent splitting off of the intermediarily introduced blocking groups with liberation of the finally desired hydroxy groups likewise can be accomplished according to methods generally known to persons skilled in the art. Thus, the blocking groups can be split off without an additional special reaction stage during the processing and isolation of the reaction products. However, this splitting-off reaction can also be conducted in the usual way in a separate reaction stage. Acyl blocking groups can be split off, for example, by alkaline hydrolysis, and acetal, ketal, or ether blocking groups can be split off by acidic hydrolysis.

When the compounds of Formula I of this invention are to be prepared by way of process version (b), the acylation of the aromatic amino group in the corresponding starting compound of Formula IIB likewise takes place according to known methods, for example, by reacting the amine in an inert solvent, e.g., pyridine, DMA (dimethylacetamide), DMF (dimethylformamide) and similar compounds at temperatures of 0° C. to room temperature with a reactive $R'_5$.CO-acid derivative, preferably with the corresponding acid halogenide, especially acid chloride, or also with a corresponding acid anhydride, preferably in the presence of an acidic catalyst, such as, for example, $H_2SO_4$.

In a modification of process version (a), to avoid secondary products, it may be advantageous to effect the introduction of the first amide group in a previous precursory stage. In such a case, a monoamide of Formula IIC (which is identical to the primary product of process version [a]) is suitably utilized as the starting compound for producing the compounds of Formula I of this invention. This monoamide is amidated, as described above, with a base of Formula IV. The optionally following alkylation of the aromatic acylamino group and the splitting off of any hydroxy blocking groups present likewise takes place as indicated above.

The starting compound of Formula IIA can be obtained from the known 5-amino-2,4,6-triiodoisophthalic acid dichloride wherein first the amino group is conventionally acylated with the corresponding acid chloride $R'_5$-COCl (wherein $R'_5$ is as defined above) in a suitable solvent, e.g., dimethylacetamide or dimethylformamide at 0°-10° C.

If $R_6$ is to be an optionally hydroxylated lower alkyl residue, the N-alkylation, as described above, likewise is performed according to conventional methods. If $R_6$ in the process product of Formula I is an unsubstituted alkyl group, e.g., the methyl group, it is advantageous that this group be already contained in the starting compound of Formula IIA. If $R_6$ in the process product of Formula I, however, is hydroxyalkyl, then the introduction should occur suitably after the amidation reactions. However, if the residue $R_6$ is to be already present in the starting compound of Formula IIA, then it is advantageous to intermediarily block the hydroxy groups contained in $R_6$.

The starting compound of Formula IIB can be obtained, for example, also from 5-amino-2,4,6-triiodoisophthalic acid dichloride, by amidating the two acid chloride groups as described above for the reaction IIA→I, or from the monomethyl ester of 5-nitroisophthalic acid, as described in Example 7, for example, in connection with 5-amino-2,4,6-triiodoisophthalic acid [(2,3-diacetoxypropyl)-(2,3-diacetoxy-N-methylpropyl)]diamide.

The starting compound of Formula IIC is suitably also obtained from the readily accessible monomethyl ester of 5-nitroisophthalic acid. By aminolysis of the methyl ester group, the amide residue —N.R$_1$R$'_2$ or —N.R$_3$R$'_4$ is introduced first. If any hydroxy groups present in the amide residue are in the free form, they are preferably conventionally blocked, for example, as the O-acetate. The subsequent reduction of the nitro group to the aromatic amino group likewise can be performed according to known methods, for example, with Raney nickel in the presence of a lower alcohol, such as methanol or ethanol under normal or elevated pressure. The thus-obtained 5-aminoisophthalic acid monoamide is then triiodinated in the usual way, and the free carboxy group is converted into the acid halogenide group, preferably into the —COCl-group. Subsequently the aromatic amino group is N-acylated to form the starting compound of Formula IIC, e.g., in a conventional fashion with a reactive $R'_5$-acid derivative, as described above.

The compounds of Formula I of this invention are stable in solution, so that they can be sterilized in the usual way even by heating to 120° C. at a physiological pH value. The solutions, even with a high iodine concentration, have a low osmotic pressure as compared with conventional ionic X-ray contrast media. This is a prerequisite for a good local compatibility, in particular. Solutions of several of the novel compounds have a very low viscosity, which enables easy manipulation. The compounds themselves are extremely hydrophilic, which is a prerequisite for their high general compatibility.

The compounds of this invention, when subjected to animal tests using various animal species, showed a very good general compatibility and an excellent local compatibility, a very good cardiovascular compatibility, and only a low neurotoxicity. Moreover, the compounds of this invention, in an in vitro test, showed only an extremely minor interaction with proteins and only a very low membrane-damaging effect.

Because of their good pharmacological properties, the novel compounds of Formula I are excellently suitable as opacifying compounds in all fields of application of water-soluble X-ray contrast media, especially for intravasal, subarachnoid and various local applications in the same manner as known X-ray contrast agents, e.g., metrizamide.

The present invention therefore also relates to novel X-ray contrast media based on the compounds of Formula I.

Such novel X-ray contrast media can be prepared in a conventional manner, for example, by bringing the opacifying compound into a form suitable for intravenous administration, together with additives conventional in galenic pharmacy, e.g., stabilizers, such as sodium edetate, calcium disodium edetate, physiologically compatible buffers, sodium chloride, and similar compounds.

The compounds of this invention can be employed in mixture with conventional excipients, i.e., pharmaceutically acceptable organic or inorganic carrier substances suitable for parenteral or enteral application which do not deleteriously react with the active compound, for administration to a patient, e.g., mammals including humans. Suitable pharmaceutically acceptable carriers, include but are not limited to, water, salt solutions, alcohols, vegetable oils, polyethylene glycols, gelatin, lactose, amylose, magnesium stearate, viscous paraffin, perfume oil, fatty acid monoglycerides and diglycerides, pentaerythritol fatty acid esters, hydroxy methylcellulose, polyvinyl pyrrolidone, talc, etc.

For parenteral application, particularly suitable are solutions, preferably oily or aqueous solutions, as well as suspensions or emulsions. Ampoules are convenient unit dosages.

For enteral application, particularly suitable are tablet or dragees having talc and/or a carbohydrate carrier or binder or the like, the carrier preferably being lactose and/or corn starch and/or potato starch. A syrup or the like can be used wherein a sweetened vehicle is employed. Sustained release compositions can also be formulated wherein the active compound is protected with differentially degradable coatings, e.g., by microencapsulation, multiple coatings, etc.

For intravenous administration, the compounds of this invention are preferably used in aqueous solutions whereby the concentration of active compound is between about 15% by volume and about 80% by volume. Generally the amount of active agent per unit dosage is about 1 to 80 g, preferably 2 to 70 g.

The solutions have a relatively low viscosity and can be administered by intravenous injection and are furthermore distinguished by good circulatory compatibility and low toxicity.

The concentration of the novel X-ray contrast compound of this invention in an aqueous medium is entirely dependent on the method of X-ray diagnostics employed. The preferred concentrations and dosages of the novel compounds are 50–400 mg I/ml and 2–500 ml, respectively. Concentrations of 100–400 mg I/ml are especially preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

5-(S-2-Hydroxypropionylamino)-2,4,6-triiodoisophthalic Acid

[(2,3-Dihydroxy-N-methylpropyl)-(2-hydroxy-1-hydroxymethylethyl)]diamide 20.8 g. (27.2 millimoles) of 5-(S-2-acetoxypropionylamino)-2,4,6-triiodoisophthalic acid (2-hydroxy-1-hydroxymethylethyl)amide chloride is dissolved in 60 ml. of dry DMF; at room temperature, 5.8 g. (55 mmol) of 2,3-dihydroxy-N-methylpropylamine is added to the reaction mixture and the latter is heated for 3 hours to 40° C. The solvent is evaporated under vacuum, the oily residue is dissolved in 80 ml. of water, adjusted to pH 11 with 35 ml. of concentrated aqueous ammonia, and stirred for 3 hours at room temperature. The solution is then evaporated to about 50 ml. and deionized via an anion exchanger and a cation exchanger. Evaporation of the aqueous eluate yields 16.3 g.=76% of theory of the desired compound.

EXAMPLE 2

5-(S-2-Hydroxypropionylamino)-2,4,6-triiodoisophthalic Acid

[(2-Hydroxyethyl)-(2-hydroxy-1-hydroxymethylethyl)]-diamide 11.5 g. (15 mmol) of 5-(S-2-acetoxypropionylamino)-2,4,6-triiodoisophthalic acid (2-hydroxy-1-hydroxymethylethyl)-amide chloride is dissolved in 45 ml. of dry DMF; 2.94 g. (40 mmol) of ethanolamine is added thereto, and the mixture is agitated for 3 hours at room temperature. The solvent is evaporated under vacuum, the remaining oil is dissolved in 20 ml. of water and stirred with 40 ml. of aqueous concentrated ammonia for 3 hours at room temperature. The solution is then evaporated to about 30 ml. under vacuum and deionized via an anion exchanger and a cation exchanger. The evaporated, aqueous eluate yields 7.4 g.=66% of theory of the desired compound.

EXAMPLE 3

5-(S-2-Hydroxypropionylamino)-2,4,6-triiodoisophthalic Acid

[(2-Hydroxy-N-methylethyl)-(2-hydroxy-1-hydroxymethylethyl)]diamide 11.5 g. (15 mmol) of 5-(S-2-acetoxypropionylamino)-2,4,6-triiodoisophthalic acid (2-hydroxy-1-hydroxymethylethyl)-amide chloride is dissolved in 45 ml. of dry DMF; 3 g. (40 mmol) of N-methylethanolamine is added thereto and the mixture is stirred for 3 hours at room temperature. The solvent is evaporated under vacuum, the remaining oil is dissolved in 20 ml. of water and stirred with 40 ml. of concentrated aqueous ammonia for 3 hours at room temperature. The solution is then concentrated under vacuum to about 30 ml. and deionized via an anion exchanger and a cation exchanger. The evaporated aqueous eluate yields 8.6 g.=75% of theory of the desired compound.

EXAMPLE 4

5-(S-2-Hydroxypropionylamino)-2,4,6-triiodoisophthalic Acid [(2,3-Dihydroxy-N-methylpropyl)-(2,3-dihydroxypropyl)]diamide (a)

5-(S-2-Acetoxypropionylamino)-2,4,6-triiodoisophthalic Acid (2,3-Dihydroxypropyl)amide Chloride 14.2 g. (20 mmol) of 5-(S-2-acetoxypropionylamino)-2,4,6-triiodoisophthalic acid dichloride is dissolved in 60 ml. of dry DMF; at room temperature, a solution of 3.83 g. (42 mmol) of 2,3-dihydroxypropylamine, dissolved in 15 ml. of DMF, is added dropwise, and the mixture is stirred for 80 minutes. The reaction solution is then concentrated to 25 ml., stirred into 250 ml. of dioxane heated to 80° C., decanted off from the hydrochloride precipitate, concentrated to 50 ml., and stirred into 400 ml. of methylene chloride. The fine, solid precipitate is dried at 50° C. under vacuum. Yield: 10.2 g.=67% of theory.

(b)

5-(S-2-Hydroxypropionylamino)-2,4,6-triiodoisophthalic Acid [(2,3-Dihydroxy-N-methylpropyl)-(2,3-dihydroxypropyl)]diamide 10.2 g. (13.4 mmol) of 5-(S-2-acetoxypropionyl)-amino)-2,4,6-triiodoisophthalic acid (2,3-dihydroxypropyl)amide chloride is dissolved in 30 ml. of dry DMF; a solution of 2.95 g. (28.14 mmol) of 2,3-dihydroxy-N-methylpropylamine in 8 ml. of DMF is added at room temperature, and the mixture is stirred for 1 hour. The reaction solution is concentrated, the oily residue is dissolved in 50 ml. of water and agitated with 12 ml. of concentrated aqueous ammonia for 4 hours at room temperature. The mixture is then adjusted to pH 7 with hydrochloric acid, diluted to 100 ml., and deionized on 250 ml. of "Amberlite XAD-4". Yield: 7 g.=66% of theory.

EXAMPLE 5

5-(S-2-Hydroxypropionylamino)-2,4,6-triiodoisophthalic Acid [(2-Hydroxyethyl)-(tris-hydroxymethyl-methyl)]diamide (a)

5-(S-2-Acetoxypropionylamino)-2,4,6-triiodoisophthalic Acid (Tris-hydroxymethyl-methyl)amide Chloride 20 g. (28.2 mmol) of 5-(S-2-acetoxypropionyl-amino)-2,4,6-triiodoisophthalic acid dichloride is refluxed together with 6.82 g. (56.4 mmol) of tris(hydroxymethyl)-methylamine in 100 ml. of dioxane for 72 hours, filtered in the hot state, and the filtrate evaporated. Yield: 9.8 g.=43% of theory.

(b)

5-(S-2-Hydroxypropionylamino)-2,4,6-triiodoisophthalic Acid [(2-Hydroxyethyl)-(trishydroxymethyl-methyl)]diamide 2.9 g. (3.76 mmol) of 5-(S-2-acetoxypropionyl)-amino)-2,4,6-triiodoisophthalic acid (tris-hydroxymethyl-methyl)-amide chloride and 0.46 g. (7.52 mmol) of ethanolamine are stirred together in 10 ml. of dry DMF for 3 hours at room temperature. The reaction solution is then stirred into 200 ml. of methylene chloride, the precipitate is filtered off, dried, dissolved in 50 ml. of water, and deionized on 100 ml. of "Amberlite XAD-4". Yield: 1.9 g.=67% of theory.

EXAMPLE 6

5-Methoxyacetylamino-2,4,6-triiodoisophthalic Acid [(2,3-Dihydroxy-N-methylpropyl)-(2,3-dihydroxypropyl)]diamide (a) 5-Methoxyacetylamino-2,4,6-triiodoisophthalic Acid Dichloride 121.2 g. (1.6 mole) of methoxyacetic acid is dissolved in 400 ml. of dry DMF, cooled to 0° C., and within 60 minutes 116 ml. (1.6 mol) of thionyl chloride is added dropwise thereto. The mixture is stirred for 30 minutes at 10° C. and 138.3 g. (0.4 mol) of 5-amino-2,4,6-triiodoisophthalic acid dichloride is introduced into the reaction mixture and the latter is stirred for 20 hours at room temperature. The reaction solution is stirred into 10 l. of water, the precipitate is vacuum-filtered, washed with water, again stirred with water, vacuum-filtered, and dried at 50° C. under vacuum. Yield: 198 g. (0.296 mol)=74% of theory.

(b) 5-Methoxyacetylamino-2,4,6-triiodoisophthalic Acid (2,3-Dihydroxypropyl)amide Chloride 50 g. (75 mmol) of 5-methoxyacetylamino-2,4,6-triiodoisophthalic acid dichloride is dissolved in 200 ml. of dry DMF; 18 g. (97.3 mmol) of tributylamine is added thereto, the mixture is heated to 60° C., and, at this temperature, a solution of 7.5 g. (82.4 mmol) of 2,3-dihydroxypropylamine in 50 ml. of DMF is added dropwise thereto. The mixture is stirred for 2 hours at 60° C., then concentrated to 100 ml., and stirred into 1.2 l. of methylene chloride. The precipitate thus formed is vacuum-filtered, dried, refluxed twice with respectively 500 ml. of ethyl acetate, and filtered in the hot state. The evaporated filtrate yields 40.5 g. (56 mmol)=74.5% of theory of the desired product as a colorless solid.

(c) 5-Methoxyacetylamino-2,4,6-triiodoisophthalic Acid [(2,3-Dihydroxy-N-methylpropyl)-(2,3-dihydroxypropyl)]diamide 50 g. (69.2 mmol) of 5-methoxyacetylamino-2,4,6-triiodoisophthalic acid (2,3-dihydroxypropyl)amide chloride is dissolved in 150 ml. of dry DMF and, at room temperature, a solution of 7.25 g. (69.2 mmol) of 2,3-dihydroxy-N-methylpropylamine and 12.85 g. (69.2 mmol) of tributylamine in 80 ml. of DMF is introduced dropwise. After stirring for 2 hours at room temperature the mixture is concentrated to about 100 ml., and the concentrate is stirred into 2 l. of methylene chloride. The precipitate is vacuum-filtered, dried, dissolved in 250 ml. of water, the pH adjusted to 7, and the mixture is stirred with 5 g. of active carbon for 30 minutes, filtered, and the filtrate deionized on 1.5 l. of "Amberlite XAD-4". After evaporation of the aqueous eluate, the product is obtained as a colorless solid. Yield: 44.4 g. (56.05 mmol)=81% of theory.

EXAMPLE 7

(a) 5-Nitroisophthalic Acid (2,3-Dihydroxy-N-methylpropyl)monoamide 22.5 g. (100 mmol) of 5-nitroisophthalic acid monomethyl ester is refluxed for 24 hours with 20.5 g. (200 mmol) of 2,3-dihydroxy-N-methylpropylamine in 120 ml. of methanol. The reaction solution is then concentrated to about 70 ml. and 700 ml. of 1 N hydrochloric acid is added dropwise thereto, the compound thus being deposited as a solid. The product is vacuum-filtered, washed with water, and dried under vacuum at 50° C. Yield: 25 g. (83.8 mmol)=83.8% of theory.

The compound is also obtained by adding a solution of 63.3 g. (260 mmol) of 5-nitroisophthalic acid monomethyl ester chloride, dissolved in 200 ml. of acetone, at 5° C. to a solution of 30 g. (286 mmol) of 2,3-dihydroxy-N-methylpropylamine and 43.7 g. (520 mmol) of sodium bicarbonate in 200 ml. of water, and saponifying the initially formed ester amide with sodium hydroxide solution. Yield: 62.6 g. (210 mmol)=80.7% of theory.

(b) 5-Nitroisophthalic Acid (2,3-Dihydroxy-N-methylpropyl)amide Methyl Ester 25 g. (83.8 mmol) of 5-nitroisophthalic acid (2,3-dihydroxy-N-methylpropyl)monoamide is dissolved in 100 ml. of methanol; 0.3 ml. (5.5 mmol) of concentrated $H_2SO_4$ is added to the mixture, and the latter is stirred for 5 hours at room temperature. The reaction solution is then buffered with 1 g. (12.8 mmol) of sodium acetate, concentrated to about 30 ml., and the concentrate is stirred into 300 ml. of water. The precipitate is vacuum-filtered, washed with water, and dried. Yield: 25 g. (80.5 mmol)=96% of theory.

The compound can also be prepared from 5-nitroisophthalic acid monomethyl ester chloride:

30 g. (123.2 mmol) of 5-nitroisophthalic acid monomethyl ester chloride is dissolved in 100 ml. of dioxane, and a solution of 13 g. (123.2 mmol) of 2,3-dihydroxy-N-methylpropylamine and 22.8 g. (123.2 mmol) of tributylamine in 80 ml. of dioxane is added dropwise thereto. After 5 hours of agitation at room temperature, the solution is concentrated to about 80 ml. and stirred into 500 ml. of water. The precipitate is vacuum-filtered, washed with water, and dried.

Yield: 33.5 g. (107.2 mmol)=87% of theory.

(c) 5-Nitroisophthalic Acid [(2,3-Dihydroxypropyl)-(2,3-dihydroxy-N-methylpropyl)]diamide 30 g. (96.1 mmol) of 5-nitroisophthalic acid (2,3-dihydroxy-N-methylpropyl)amide methyl ester is refluxed in 150 ml. of methanol together with 10.5 g. (115.3 mmol) of 2,3-dihydroxypropylamine for 20 hours. The reaction solution is evaporated and the remaining oil is used in the subsequent stage without further purification. The reaction is quantitative as determined by thin-layer chromatography.

(d) 5-Nitroisophthalic Acid [(2,3-Diacetoxypropyl)-(2,3-diacetoxy-N-methylpropyl)]diamide 36 g. (96 mmol) of 5-nitroisophthalic acid [(2,3-dihydroxypropyl)-(2,3-dihydroxy-N-methylpropyl)]diamide is dissolved in a mixture of 70 ml. of glacial acetic acid +70 ml. of acetic anhydride; 0.5 ml. (9.2 mmol) of concentrated $H_2SO_4$ is added thereto, and the mixture is stirred at room temperature for 5 hours. The reaction solution is then buffered with 1.5 g. (18.3 mmol) of sodium acetate, concentrated, and the residue stirred into 500 ml. of water. The precipitate is vacuum-filtered, washed with water, and dried. Yield: 47.6 g. (88.3 mmol)=92% of theory.

(e) 5-Amino-2,4,6-triiodoisophthalic Acid [(2,3-Diacetoxypropyl)-(2,3-diacetoxy-N-methylpropyl)]diamide 20 g. (37.1 mmol) of 5-nitroisophthalic acid [(2,3-diacetoxypropyl)-(2,3-diacetoxy-N-methylpropyl)]diamide is dissolved in 120 ml. of methanol, combined with 1.5 g. of Raney nickel, and hydrogenated for 3 hours at room temperature under a hydrogen pressure of 100 atmospheres. The catalyst is filtered off, the filtrate is heated to 80° C.; 50 ml. of 2 N hydrochloric acid is added thereto and, during the course of 1 hour, 66.7 ml. (133.3 mmol) of 2 N $NaICl_2$ solution is added dropwise. The mixture is stirred for 3 hours at 80° C. Upon cooling to room temperature, the product is separated as a solid. Yield: 23.5 g. (26.5 mmol)=71.3% of theory.

(f) 5-Methoxyacetylamino-2,4,6-triiodoisophthalic Acid [(2,3-Dihydroxypropyl)-(2,3-dihydroxy-N-methylpropyl)]diamide 10 g. (113 mmol) of methoxyacetic acid is dissolved in 50 ml. of DMA, cooled to 0° C., and at 0°–5° C., 8.2 ml. (113 mmol) of thionyl chloride is added dropwise. The solution is stirred for 1 hour at 10° C., then 50 g. (56.4 mmol) of 5-amino-2,4,6-triiodoisophthalic acid [(2,3-diacetoxypropyl)-(2,3-diacetoxy-N-methylpropyl)]diamide is introduced, and the mixture is stirred for 20 hours at room temperature. The solution is evaporated and the residue stirred into 1 l. of water. The precipitate is vacuum-filtered, washed with water, suspended in 300 ml. of water, and stirred at 50° C. with concentrated aqueous ammonia until a clear solution evolves. The latter is evaporated, the residue dissolved in 250 ml. of water, the solution adjusted to pH 7 and deionized on 1.5 l. of the adsorber "Amberlite XAD-4". Yield: 35 g. (44.2 mmol)=78.4% of theory.

EXAMPLE 8

(a) 5-Nitroisophthalic Acid (2,3-Diacetoxy-N-methylpropyl)monoamide 29.8 g. (100 mmol) of 5-nitroisophthalic acid (2,3-dihydroxy-N-methylpropyl)monoamide is dissolved in a mixture of 50 ml. of glacial acetic acid +50 ml. of acetic anhydride. The mixture is combined with 0.3 ml. (5.5 mmol) of concentrated $H_2SO_4$ and stirred for 3 hours at room temperature. The solution is then buffered with 1 g. (12.8 mmol) of sodium acetate, concentrated, and stirred into 1 l. of water. The product is thus obtained as a solid precipitate, which is vacuum-filtered, washed with water, and dried at 50° C. under vacuum. Yield: 35.2 g. (92 mmol)=92% of theory.

(b) 5-Amino-2,4,6-triiodoisophthalic Acid (2,3-Diacetoxy-N-methylpropyl)monoamide 20 g. (52.3 mmol) of 5-nitroisophthalic acid (2,3-diacetoxy-N-methylpropyl)monoamide is hydrogenated in 100 ml. of methanol in the presence of 1.5 g. of Raney nickel at room temperature for 3 hours under a hydrogen pressure of 100 at. The catalyst is then filtered off, the filtrate is heated to 80° C., combined with 50 ml. of 1 N hydrochloric acid, and then during the course of 1 hour 86.5 ml. (173 mmol) of 2 N $NaICl_2$ solution is added dropwise thereto. The mixture is stirred for 2 hours at 80° C. and cooled to room temperature. The product is separated as a solid. Yield: 27.8 g. (38 mmol)=73% of theory.

The nitro group can also be reduced under normal pressure in the presence of 10% Pd/C catalyst. For this purpose, 20 g. (52.3 mmol) of 5-nitroisophthalic acid (2,3-diacetoxy-N-methylpropyl)monoamide is dissolved in 100 ml. of methanol, 1.5 g. of 10% Pd/C catalyst is added thereto, and the mixture is hydrogenated for 5 hours at room temperature. After separation of the catalyst, the hydrogenation solution is iodinated in the above-described way. Yield: 26 g. (35.6 mmol)=68% of theory.

(c) 5-Amino-2,4,6-triiodoisophthalic Acid (2,3-Diacetoxy-N-methylpropyl)amide Chloride 109.5 g. (150 mmol) of 5-amino-2,4,6-triiodoisophthalic acid (2,3-diacetoxy-N-methylpropyl)monoamide is dissolved in 600 ml. of toluene, refluxed on a water trap until the separation of water has ceased, then cooled to 40° C., and 33.3 g. (160 mmol) of PCl$_5$ is introduced in incremental portions. The suspension is subsequently stirred for 2 hours at 60° C. and for 5 hours at room temperature, the toluene is then distilled off under reduced pressure, and the solid residue is purified by extraction with methylene chloride and petroleum ether. Yield: 96.5 g. (129 mmol)=86% of theory.

(d) 5-Methoxyacetylamino-2,4,6-triiodoisophthalic Acid (2,3-Diacetoxy-N-methylpropyl)amide Chloride 30 g. (0.4 mol) of methoxyacetic acid is dissolved in 100 ml. of DMA, cooled to 0° C., and at 0°–5° C. 29 ml. (0.4 mol) of thionyl chloride is added dropwise to the reaction mixture. The solution is then stirred for 1 hour at 10° C. and then 150 g. (0.2 mol) of 5-amino-2,4,6-triiodoisophthalic acid (2,3-diacetoxy-N-methylpropyl)amide chloride is introduced, and the mixture stirred for 15 hours at room temperature. The reaction solution is concentrated under reduced pressure, the remaining oil is stirred into 3 l. of methylene chloride, the precipitate is vacuum-filtered, extracted with petroleum ether, and dried.

Yield: 133 g. (162 mmol)=81% of theory.

(e) 5-Methoxyacetylamino-2,4,6-triiodoisophthalic Acid [(2,3-Dihydroxypropyl)-(2,3-dihydroxy-N-methylpropyl)]diamide 50 g. (61 mmol) of 5-methoxyacetylamino-2,4,6-triiodoisophthalic acid (2,3-diacetoxy-N-methylpropyl)amide chloride is dissolved in 150 ml. of dry DMF, and at room temperature a solution of 6.4 g. (70 mmol) of 2,3-dihydroxypropylamine and 11.3 g. (61 mmol) of tributylamine in 80 ml. of DMF is added dropwise. After 2 hours of stirring at room temperature the mixture is concentrated to about 100 ml., and the concentrate is stirred into 2 l. of methylene chloride. The precipitate is vacuum-filtered, dried, dissolved in 300 ml. of water, stirred for 2 hours at 50° C. with 50 ml. of concentrated aqueous ammonia, extensively evaporated, again dissolved in 300 ml. of water, adjusted to neutral, and deionized on 1.5 l. of the adsorber "Amberlite XAD-4". Yield: 38 g. (48 mmol)=78.7% of theory.

EXAMPLE 9

5-Methoxyacetylamino-2,4,6-triiodoisophthalic Acid [(2,3-Dihydroxy-N-methylpropyl)-(2-hydroxy-1-hydroxymethylethyl)]diamide (a) 5-Methoxyacetylamino-2,4,6-triiodoisophthalic Acid (2-Hydroxy-1-hydroxymethylethyl)amide Chloride 50 g. (75 mmol) of 5-methoxyacetylamino-2,4,6-triiodoisophthalic acid dichloride is dissolved in 200 ml. of dry DMF and, at room temperature, a solution of 14.3 g. (157 mmol) of 1,3-dihydroxypropylamine in 50 ml. of dry DMF is added dropwise. The temperature rises temporarily to 45° C. The mixture is stirred for 1 hour at room temperature. The reaction solution is concentrated to 100 ml. and stirred into 800 ml. of dioxane heated to 80° C., thus obtaining the hydrochloride of 1,3-dihydroxypropylamine as an oily precipitate. The dioxane solution is decanted off, evaporated to a concentrate, and the latter stirred into 1 l. of methylene chloride. The product is thus precipitated as a solid; it is vacuum-filtered and dried under vacuum at 50° C. Yield: 39.8 g. (55.1 mmol)=73.4% of theory.

(b) 5-Methoxyacetylamino-2,4,6-triiodoisophthalic Acid [(2,3-Dihydroxy-N-methylpropyl)-(2-hydroxy-1-hydroxymethylethyl)]diamide 30.7 g. (42.5 mmol) of 5-methoxyacetylamino-2,4,6-triiodoisophthalic acid (2-hydroxy-1-hydroxymethylethyl)amide chloride is dissolved in 200 ml. of dry DMF and, at room temperature, a solution of 10 g. (89 mmol) of 2,3-dihydroxy-N-methylpropylamine in 40 ml. of dry DMF is added dropwise. The mixture is stirred for 3 hours at room temperature; then the reaction solution is concentrated to about 80 ml. and dropped into 1 l. of methylene chloride. The flaky precipitate is vacuum-filtered, dissolved in 100 ml. of water, and residues of organic solvent are removed by renewed evaporation. Finally, the aqueous solution is deionized on "Amberlite XAD-4". Yield: 23.3 g (29.5 mmol)=69% of theory.

EXAMPLE 10

5-(N-Methoxyacetyl-N-methylamino)-2,4,6-triiodoisophthalic Acid [(2,3-Dihydroxy-N-methylpropyl)-(2,3-dihydroxypropyl)]diamide (a) 5-(N-Methoxyacetyl-N-methylamino)-2,4,6-triiodoisophthalic Acid Dichloride 30 ml. (400 mmol) of methoxyacetic acid is dissolved in 100 ml. of DMA, cooled to 0° C., and 29 ml. (400 mmol) of SOCl$_2$ is added dropwise. The mixture is stirred for 30 minutes at this temperature, a solution of 61 g. (100 mmol) of 5-methylamino-2,4,6-triiodoisophthalic acid dichloride in 200 ml. of DMA is added dropwise thereto, and the reaction solution is stirred for 20 hours at room temperature. Then, the solution is stirred into 4 l. of water, the precipitate is vacuum-filtered, dissolved in 2 l. of ethyl acetate, successively extracted with respectively 250 ml. of saturated bicarbonate solution, saturated sodium chloride solution, and water; the ethyl acetate phase is dried over Na$_2$SO$_4$ and evaporated. Yield: 61.4 g. (90 mmol)=90% of theory.

(b) 5-(N-Methoxyacetylmethylamino)-2,4,6-triiodoisophthalic Acid (2,3-Dihydroxypropyl)amide Chloride 58.3 g. (85.5 mmol) of 5-(N-methoxyacetyl-N-methylamino)-2,4,6-triiodoisophthalic acid dichloride is dissolved in 200 ml. of dry DMF and, at room temperature, a solution of 16.4 g. (180 mmol) of 2,3-dihydroxypropylamine in 50 ml. of DMF is added dropwise. The reaction solution is stirred for 1 hour, then concentrated to 100 ml., stirred into 800 ml. of dioxane heated to 80° C., decanted off from the precipitated amine hydrochloride; the dioxane solution is concentrated and stirred into 1 l. of methylene chloride. The precipitate is vacuum-filtered, washed with methylene chloride, and dried at 50° C. under vacuum.

Yield: 53.8 g. (73 mmol)=85.4% of theory.

(c) 5-(N-Methoxyacetyl-N-methylamino)-2,4,6-triiodoisophthalic Acid [(2,3-Dihydroxy-N-methylpropyl)-(2,3-dihydroxypropyl)]diamide 53.8 g. (73 mmol) of 5-(N-methoxyacetyl-N-methylamino)-2,4,6-triiodoisophthalic acid (2,3-dihydroxypropyl)amide chloride, dissolved in 300 ml. of dry DMF, is combined at room temperature with a solution of 18 g. (171 mmol) of 2,3-dihydroxy-N-methylpropylamine in 50 ml. of DMF. After 1 hour of stirring at room temperature, the mixture is concentrated to 100 ml. and stirred into 1 l. of methylene chloride, thus producing an oily precipitate which is dissolved in water and deionized on "Amberlite XAD-4". Yield: 49 g. (61 mmol)=83.6% of theory.

EXAMPLE 11

5-(N-Methoxyacetyl-N-methylamino)-2,4,6-triiodoisophthalic Acid [(2,3-Dihydroxy-N-methylpropyl)-(2-hydroxy-1-hydroxymethylethyl)]diamide

(a) 5-(N-Methoxyacetyl-N-methylamino)-2,4,6-triiodoisophthalic Acid (2-Hydroxy-1-hydroxymethylethyl)-amide Chloride 68.2 g. (100 mmol) of 5-(N-methoxyacetyl-N-methylamino)2,4,6-triiodoisophthalic acid dichloride is heated together with 22.8 g. (250 mmol) of 1,3-dihydroxypropylamine (serinol) in 400 ml. of dioxane for 10 hours to 60° C. The content of the reactor flask is filtered in the hot state, and the filtrate is concentrated to 100 ml. The product crystallizes from this solution. Yield: 54 g. (73.3 mmol)=73.3% of theory.

(b) 5-(N-Methoxyacetyl-N-methylamino)-2,4,6-triiodoisophthalic Acid [(2,3-Dihydroxy-N-methylpropyl)-(2-hydroxy-1-hydroxymethylethyl)]diamide 20 g. (27.2 mmol) of 5-(N-methoxyacetyl-N-methylamino)-2,4,6-triiodoisophthalic acid (2-hydroxy-1-hydroxymethylethyl)amide chloride is dissolved in 80 ml. of dry DMF; a solution of 5.72 g. (54.4 mmol) of 2,3-dihydroxy-N-methylpropylamine in 20 ml. of DMF is added dropwise, and the mixture is stirred for 1 hour at room temperature. The reaction solution is concentrated to 50 ml., stirred into 500 ml. of methylene chloride, the precipitate is separated, dissolved in 150 ml. of water, and deionized on approximately 600 ml. of the adsorber "Amberlite XAD-4". Yield: 17 g. (21 mmol)=77.5% of theory.

EXAMPLE 12

5-(N-Acetyl-2-hydroxyethylamino)-2,4,6-triiodoisophthalic Acid [(2,3-Dihydroxypropyl)-(2-hydroxy-1-hydroxymethylethyl)]diamide

(a) 5-Acetylamino-2,4,6-triiodoisophthalic Acid (2-Hydroxy-1-hydroxymethylethyl)amide Chloride 50 g. (78.4 mmol) of 5-acetylamino-2,4,6-triiodoisophthalic acid dichloride is dissolved in 70 ml. of DMF; the solution is diluted with 500 ml. of dioxane, heated to 60° C., and, at this temperature, 15 g. (165 mmol) of 1,3-dihydroxypropylamine (serinol), dissolved in 70 ml. of DMF, is introduced dropwise. After 30 minutes the warm reaction solution is decanted off from the precipitate, the latter is decocted with 150 ml. of dioxane, the dioxane solutions are combined, evaporated, and the remaining oil is stirred into 800 ml. of methylene chloride. The thus-obtained precipitate is vacuum-filtered and dried at 50° C. under vacuum. Yield: 38 g. (54 mmol)=69% of theory.

(b) 5-Acetylamino-2,4,6-triiodoisophthalic Acid [(2,3-Dihydroxypropyl)-(2-hydroxy-1-hydroxymethylethyl)]diamide 8.84 g. (97 mmol) of 2,3-dihydroxypropylamine is dissolved in 85 ml. of DMF; 30.5 g. (44 mmol) of 5-acetylamino-2,4,6-triiodoisophthalic acid (2-hydroxy-1-hydroxy-methylethyl)amide chloride is added thereto, and the mixture is stirred for one hour at room temperature. The reaction solution is evaporated, the remaining oil is stirred into 800 ml. of methylene chloride, the precipitate is separated, dissolved in water, and deionized on 600 ml. of "Amberlite XAD-4". Yield: 25 g. (33.5 mmol)=76% of theory.

(c) 5-(N-Acetyl-2-hydroxyethylamino)-2,4,6-triiodoisophthalic Acid [(2,3-Dihydroxypropyl)-(2-hydroxy-1-hydroxymethylethyl)]diamide 21.7 g. (29 mmol) of 5-acetylamino-2,4,6-triiodoisophthalic acid [(2,3-dihydroxypropyl)-(2-hydroxy-1-hydroxymethylethyl)]diamide is dissolved in 17.4 ml. (87 mmol) of 5 N NaOH at room temperature; 7.25 g. (58 mmol) of bromoethanol is added thereto and the mixture is stirred at room temperature for 5 hours. The reaction solution is then adjusted to pH 7 with hydrochloric acid, evaporated, the residue taken up in ethanol, the undissolved salt is filtered off, the filtrate is evaporated, and the residue is dissolved in water and deionized on "Amberlite XAD-4". Yield: 16 g. (20.2 mmol)=70% of theory.

EXAMPLE 13

5-(N-Acetyl-2-hydroxyethylamino)-2,4,6-triiodoisophthalic Acid
[(2,3-Dihydroxy-N-methylpropyl)-(2-hydroxy-1-hydroxymethylethyl)]diamide (a) 5-Acetylamino-2,4,6-triiodoisophthalic Acid
[(2,3-Dihydroxy-N-methylpropyl)-(2-hydroxy-1-hydroxymethylethyl)]diamide 28.6 g. (41.3 mmol) of 5-acetylamino-2,4,6-triiodoisophthalic acid (2-hydroxy-1-hydroxymethylethyl)amide chloride is added at room temperature to a solution of 9.8 g. (86.7 mmol) of 2,3-dihydroxy-N-methylpropylamine in 30 ml. of dry DMF and agitated for 3 hours at room temperature. The reaction solution is then stirred into 800 ml. of methylene chloride, the precipitate is separated, dissolved in water, and deionized on "Amberlite XAD-4". Yield: 18.5 g. (24.3 mmol)=59% of theory.

(b) 5-(N-Acetyl-2-hydroxyethylamino)-2,4,6-triiodoisophthalic Acid
[(2,3-Dihydroxy-N-methylpropyl)-(2-hydroxy-1-hydroxymethylethyl)]-diamide 10.6 g. (13.9 mmol) of 5-acetylamino-2,4,6-triiodoisophthalic acid [(2,3-dihydroxy-N-methylpropyl)-(2-hydroxy-1-hydroxymethylethyl)]diamide is dissolved in 8.4 ml. (42 mmol) of 5 N NaOH; 3.5 g. (28.2 mmol) of bromoethanol is added thereto and the reaction solution is stirred for 5 hours at room temperature and then diluted to 50 ml., adjusted to pH 7 with hydrochloric acid, evaporated, and the residue taken up in 50 ml. of ethanol. The product is separated from undissolved salt, the ethanol solution is concentrated, the residue dissolved in water and deionized on "Amberlite XAD-4". Yield: 7.5 g. (9.3 mmol)=67% of theory.

EXAMPLE 14

5-Acetylamino-2,4,6-triiodoisophthalic Acid
[(Trishydroxymethylmethyl)-(2-hydroxy-1-hydroxymethylethyl)]-diamide 25 g. (32 mmol) of 5-acetylamino-2,4,6-triiodoisophthalic acid (2-hydroxy-1-hydroxymethylethyl)amide chloride and 38.8 g. (320 mmol) of tris(hydroxymethyl)methylamine are refluxed in 500 ml. of dioxane for 8 hours. The reaction solution is then evaporated, the residue is dissolved under heating in 100 ml. of DMF, and the solution is stirred into 800 ml. of dioxane heated to 90° C. The hydrochloride of the amine is thus precipitated. The solution is decanted, evaporated, taken up in 300 ml. of water, adjusted to pH 7 with hydrochloric acid, and deionized on "Amberlite XAD-4". Yield: 17.5 g. (22.5 mmol)=70.4% of theory.

EXAMPLE 15

5-(N-Acetyl-2-hydroxyethylamino)-2,4,6-triiodoisophthalic Acid
[(2,3-Dihydroxypropyl)-(2,3-dihydroxy-N-methylpropyl)]diamide (a) 5-Acetylamino-2,4,6-triiodoisophthalic Acid
[(2,3-Dihydroxypropyl)-(2,3-dihydroxy-N-methylpropyl)]diamide 44.4 g. (50 mmol) of 5-amino-2,4,6-triiodoisophthalic acid [(2,3-diacetoxypropyl)-(2,3-diacetoxy-N-methylpropyl)]diamide is dissolved in 100 ml. of DMA; at 10° C., 7 g. (89.3 mmol) of acetyl chloride is added dropwise, and the reaction solution is stirred for 20 hours at room temperature, whereafter it is evaporated, the oil is suspended in 100 ml. of water and stirred with 50 ml. of concentrated aqueous ammonia for 5 hours at room temperature until a clear solution has been produced. The latter is evaporated to an oil; the oil is stirred into 500 ml. of methylene chloride, the solid precipitate is filtered off, dried, dissolved in water, and deionized on 1 l. of the adsorber "Amberlite XAD-4".
Yield: 29 g. (38 mmol)=76% of theory.

(b) 5-(N-Acetyl-2-hydroxyethylamino)-2,4,6-triiodoisophthalic Acid
[(2,3-dihydroxypropyl)-(2,3-dihydroxy-N-methylpropyl)]diamide 20 g. (26.3 mmoL) of 5-acetylamino-2,4,6-triiodoisophthalic acid [(2,3-dihydroxypropyl)-(2,3-dihydroxy-N-methylpropyl)]diamide is dissolved in 40 ml. (200 mmol) of 5 N NaOH. 6.6 g. (53 mmol) of bromoethanol is added thereto and the reaction solution is stirred for 5 hours at room temperature. The solution is then neutralized with hydrochloric acid under cooling, evaporated, and the residue is taken up in ethanol, filtered off from the insoluble salt, the filtrate is evaporated, dissolved in water, and deionized on 800 ml. of the adsorber "Amberlite XAD-4". Yield: 12.7 g. (15.75 mmol)=63% of theory.

EXAMPLE 16

Preparing a ready-to-use solution for urography and angiography:

(a) The solution contains 300 mg. iodine per ml. composition:

| | |
|---|---|
| 5-Methoxyacetylamino-2,4,6-triiodoisophthalic acid [(2,3-dihydroxy-N—methyl-propyl)-(2,3-dihydroxypropyl)]-diamide | 62,340 g |
| Calcium disodium edetate | 0,010 g |
| Sodium hydroxide (0,1 n) to make pH 7,2 | |
| water for injection (twice distilled) | ad 100 ml |

The solution is filled into ampoules or multivials and sterilized at 120° C.

(b) The solution contains 370 mg iodine per ml. composition:

| | |
|---|---|
| 5-Methoxyacetylamino-2,4,6-triiodoisophthalic acid [(2,3-dihydroxy-N—methyl-propyl)-(2,3-dihydroxypropyl)]-diamide | 76,885 g |
| Calcium disodium edetate | 0,010 g |
| Sodium hydroxide (0,1 n) to make pH 7,2 | |
| water for injection (twice distilled) | ad 100 ml |

The solution is filled into ampoules or multivials and sterilized at 120° C.

EXAMPLE 17

Preparing a ready-to-use solution for gastrography:
The solution contains 370 mg iodine per ml. Composition:

| | |
|---|---|
| 5-Methoxyacetylamino-2,4,6-triiodoisophthalic acid-[(2,3-dihydroxy-N—methylpropyl)-(2,3-dihydroxy-propyl)]-diamid | 76,885 g |

| | |
|---|---|
| -continued | |
| Aniseed-oil | 0,140 g |
| Polyoxyethylen-sorbitan-mono-oleat | 0,750 g |
| Twice-distilled water | ad 100 ml. |

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A triiodinated isophthalic acid diamide of the formula

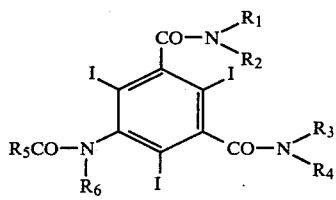

wherein
the amide residues —CO—N.R$_1$R$_2$ and —CO—N.R$_3$R$_4$ are different from each other and
R$_1$ is hydrogen or C$_{1-6}$ alkyl,
R$_2$ is mono- or polyhydroxyalkyl,
R$_3$ is hydrogen or C$_{1-6}$ alkyl,
R$_4$ is mono- or polyhydroxyalkyl,
R$_5$ is C$_{1-6}$ alkyl or monohydroxy-C$_{1-6}$-alkyl or C$_{1-3}$-alkoxy-C$_{1-3}$-alkyl, and
R$_6$ is hydrogen or C$_{1-6}$ alkyl or mono-.

2. 5-Methoxyacetylamino-2,4,6-triiodoisophthalic acid [(2,3-dihydroxy-N-methylpropyl)-(2,3-dihydroxypropyl)]diamide, a compound of claim 1.

3. 5-(S-2-Hydroxypropionylamino)-2,4,6-triiodoisophthalic acid [(2,3-dihydroxy-N-methylpropyl)-(2,3-dihydroxypropyl)]diamide, a compound of claim 1.

4. 5-Methoxyacetylamino-2,4,6-triiodoisophthalic acid [(2,3-dihydroxy-N-methylpropyl)-(2-hydroxy-1-hydroxymethylethyl)]diamide, a compound of claim 1.

5. The compound of claim 1, wherein at least one of R$_1$, R$_2$, R$_3$ or R$_4$ is dihydroxyalkyl.

6. A compound of claim 5, wherein at least one of R$_1$ or R$_2$ is dihydroxyalkyl and at least one of R$_3$ and R$_4$ is dihydroxyalkyl.

7. A compound of claim 5 or 6 wherein all alkyl moieties in R$_1$, R$_2$, R$_3$ and R$_4$ have three carbon atoms.

8. A pharmaceutical composition for use as an X-ray contrast agent comprising a radiopaque amount of a compound of Claim 1 and a pharmaceutically acceptable carrier.

9. A method of conducting a radiological examination of a patient which comprises administering to the patient a radiopaque amount of a compound of claim 1.

10. 5-Acetylamino-2,4,6-triiodoisophthalic Acid [(2,3-dihydroxypropyl)-(2,3-dihydroxy-N-methylpropyl)]diamide.

11. A compound of claim 1 wherein R$_5$ is methoxymethyl 1-hydroxyethyl or methyl.

12. A compound of claim 1, wherein R$_1$ and R$_3$ each are H or CH$_3$, and R$_2$ and R$_4$ each are —CH$_2$—CHOH—CH$_2$OH or

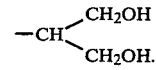

13. A composition of claim 8 wherein the carrier is pharmaceutically acceptable for angiography.

14. A method of claim 9, wherein the radiological examination is angiography.

15. A compound of claim 11, wherein R$_6$ is H or C$_{1-4}$-alkyl.

* * * * *

UNITED STATES PATENT AND TRADEMARK OFFICE
CERTIFICATE OF CORRECTION

PATENT NO. : 4,364,921
DATED : December 21, 1982
INVENTOR(S) : ULRICH SPECK ET AL It is certified that error appears in the above-identified patent and that said Letters Patent is hereby corrected as shown below:

Column 19, line 43: reads "$R_6$ is hydrogen or $C_{1-6}$ alkyl or mono-"
should read -- $R_6$ is hydrogen or $C_{1-6}$ alkyl --

Signed and Sealed this

First Day of March 1983

[SEAL]

Attest:

GERALD J. MOSSINGHOFF

Attesting Officer          Commissioner of Patents and Trademarks

UNITED STATES PATENT AND TRADEMARK OFFICE

CERTIFICATE EXTENDING PATENT TERM
UNDER 35 U.S.C. § 156

PATENT NO. : 4,364,921

ISSUED : December 21, 1982

INVENTOR(S) : Ulrich Speck, et al.

PATENT OWNER : Schering Aktiengesellschaft

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of Five Years from the original expiration date of the patent, March 6, 2000, with all rights pertaining thereto as provided by 35 U.S.C. § 156(b).

I have caused the seal of the Patent and Trademark Office to be affixed this 17th day of March 1997.

Bruce A. Lehman
Assistant Secretary of Commerce and
  Commissioner of Patents and Trademarks